US009050432B2

(12) United States Patent
Lu et al.

(10) Patent No.: US 9,050,432 B2
(45) Date of Patent: Jun. 9, 2015

(54) MEDICAL APPARATUS FOR ATOMIZING WATER, GAS, AND LIQUID MEDICATION

(71) Applicants: Sheng-I Lu, Kaohsiung (TW); Johnny En-Chih Wu, Kaohsiung (TW)

(72) Inventors: Sheng-I Lu, Kaohsiung (TW); Johnny En-Chih Wu, Kaohsiung (TW)

( * ) Notice: Subject to any disclaimer, the term of this patent is extended or adjusted under 35 U.S.C. 154(b) by 199 days.

(21) Appl. No.: 13/855,740

(22) Filed: Apr. 3, 2013

(65) Prior Publication Data

US 2014/0299124 A1 Oct. 9, 2014

(51) Int. Cl.
| | |
|---|---|
| *A61M 37/00* | (2006.01) |
| *A61M 11/06* | (2006.01) |
| *A61M 11/02* | (2006.01) |
| *A61M 11/04* | (2006.01) |
| *A61M 35/00* | (2006.01) |
| *A61L 9/03* | (2006.01) |
| *A61M 15/00* | (2006.01) |

(52) U.S. Cl.

CPC ............... *A61M 11/06* (2013.01); *A61M 11/02* (2013.01); *A61M 35/00* (2013.01); *A61M 37/00* (2013.01); *A61L 9/03* (2013.01); *A61M 2202/0208* (2013.01); *A61M 2202/0225* (2013.01); *A61M 2202/0266* (2013.01); *A61M 2205/502* (2013.01); *A61M 11/042* (2014.02); *A61M 15/0003* (2014.02)

(58) Field of Classification Search

CPC ..................... A61M 15/0003; A61M 16/0012; A61M 16/10; A61M 16/16; A61M 16/164; A61M 16/18; A61M 16/127; A61M 11/02; A61M 35/00; A61M 35/003; A61M 37/00; A61H 33/02

USPC ............. 128/203.25–203.27, 200.14, 200.19, 128/200.23, 204.24; 600/24
See application file for complete search history.

(56) References Cited

U.S. PATENT DOCUMENTS

| | | | | |
|---|---|---|---|---|
| 5,322,057 | A * | 6/1994 | Raabe et al. | 128/203.12 |
| 7,201,166 | B2 * | 4/2007 | Blaise et al. | 128/203.12 |
| 2003/0101991 | A1 * | 6/2003 | Trueba | 128/200.14 |
| 2005/0072420 | A1 * | 4/2005 | Gershteyn | 128/200.19 |

* cited by examiner

*Primary Examiner* — Kristen Matter

(57) ABSTRACT

A medical apparatus is provided. The medical apparatus includes a water source for supplying water to a mixer, a gas source for supplying gas to a gas reservoir, a gas output for flowing gas from the gas reservoir to the mixer to mix with water to form a first mixture, a line for carrying the first mixture, Venturi tubes on the line, medication units for containing liquid medication and communicating with the Venturi tubes respectively, a mixing device being downstream of the Venturi tubes to atomize the liquid medication and the first mixture to form a final mixture, a control panel, and an outlet for exiting the final mixture. Infected skin areas of a patient can be washed aseptically by the medical apparatus.

17 Claims, 3 Drawing Sheets

MEDICAL APPARATUS FOR ATOMIZING WATER, GAS, AND LIQUID MEDICATION

BACKGROUND OF THE INVENTION

1. Field of the Invention

The invention relates to medical apparatuses and more particularly to a medical apparatus for atomizing water, gas, and liquid medication with improved characteristics.

2. Description of Related Art

Biological extracts and its components are effectively in healing the injured tissue and decreasing the seriousness of inflammation.

Typically, a medical employee must select optimum liquid medication and adjust the amount thereof prior to administer same in a medical device to a patient. It is done manually by a single spray of the medication or an application to the injured skin of the patient. However, such methods may cause the injured tissue to be contaminated if sufficient care is not taken. Further, only the dermis is washed. Killing of viruses deep inside skin is not possible. Furthermore, such methods are labor intensive and time consuming.

As far as the present inventor is aware, there are no disclosures of medical apparatus for atomizing water, gas, and liquid medication. Thus, the need for improvement still exists.

SUMMARY OF THE INVENTION

It is therefore one object of the invention to provide a medical apparatus for atomizing water, gas, and liquid medication comprising a housing; a mixer disposed in the housing and comprising a gas reservoir; a water unit disposed externally of the housing and comprising a water source and a water line for flowing water from the water source to the mixer; a gas unit disposed externally of the housing and comprising a gas source and a gas line for flowing gas from the gas source to the gas reservoir; a gas output for flowing gas from the gas reservoir to the mixer so that gas is mixed with water to form a first mixture; a line extending out of the mixer for carrying the first mixture; a valve disposed downstream of the line; a plurality of spaced Venturi tubes disposed downstream of the valve, each of the Venturi tubes being disposed above the housing; a plurality of medication units each comprising a medication reservoir for containing a quantity of liquid medication, each respective medication unit being in fluid communication with the corresponding one of the Venturi tubes; a mixing device disposed downstream of the Venturi tubes to atomize the liquid medication and the first mixture to form a second mixture; a control panel disposed on the housing and being electrically connected to the gas reservoir, the mixer, the valve, the medication reservoirs, and the mixing device respectively for control; and an outlet disposed at an end of the line and downstream of the mixing device for exiting the second mixture.

The above and other objects, features and advantages of the invention will become apparent from the following detailed description taken with the accompanying drawings.

DETAILED DESCRIPTION OF THE INVENTION

Figure 1:
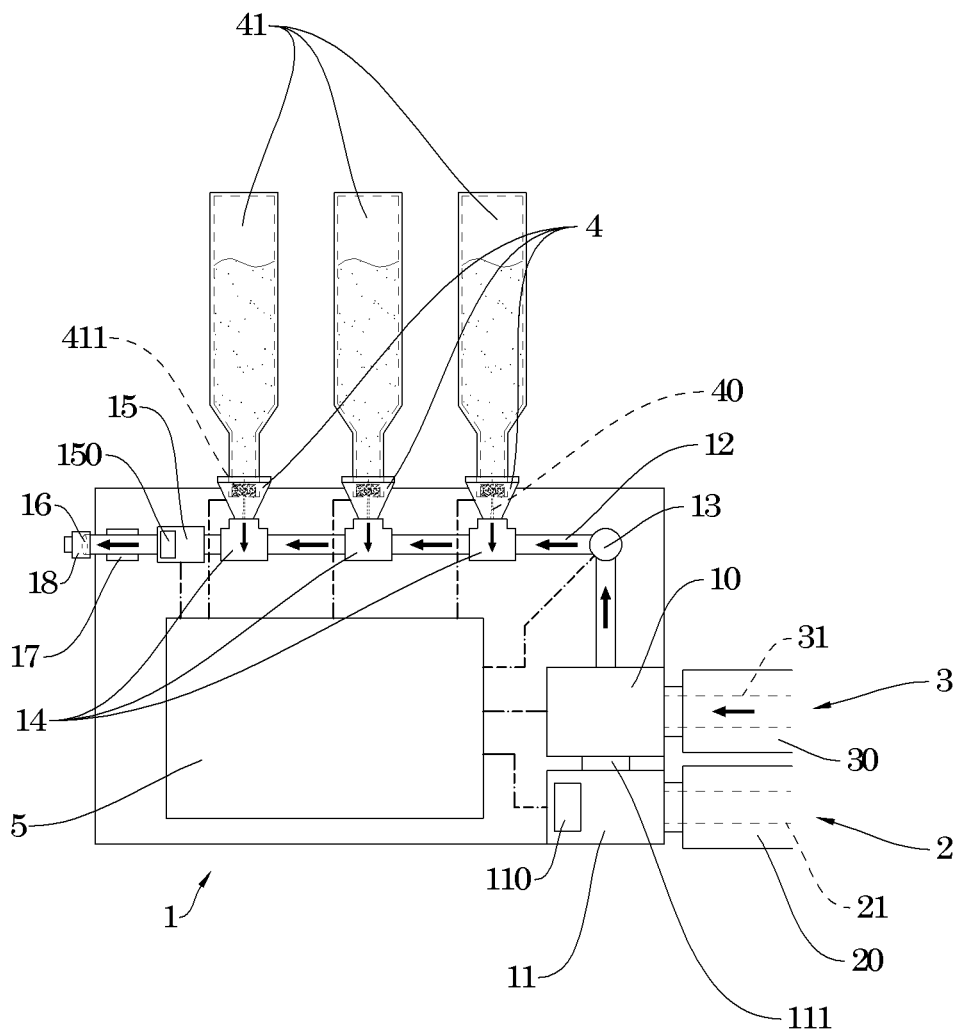
FIG. 1 schematically depicts a medical apparatus according to a first preferred embodiment of the invention.

Referring to FIG. 1, a medical apparatus in accordance with first preferred embodiment of the invention comprises the following components as discussed in detail below.

A housing 1 and a mixer 10 in the housing 1 are provided. A water unit 3 is externally of the housing 1, and a gas unit 2 is also externally of the housing 1. The water unit 3 comprises a water source 30 and a water line 31 for flowing water from the water source 30 to the mixer 10. The gas unit 2 comprises a gas source 20 and a gas line 21 for flowing gas from the gas source 20 to a gas reservoir 11 of the mixer 10. Gas is in turn fed from the gas reservoir 11 to the mixer 10 via a gas output 111. A pressure regulator 110 is provided in the gas reservoir 11. Gas and water are mixed in the mixer 10. The mixture is in turn fed to a line 12. Along the line 12, from upstream downward, there is provided a valve 13, three spaced Venturi tubes 14, and a mixing device 15. Preferably, the valve 13 is a point control valve or a long control valve.

Three medication units 4 are provided above the housing 1. Each medication unit 4 comprises a medication reservoir 41 for containing a quantity of liquid medication, a material dispensing member 40 on a bottom of the medication reservoir 41, and a rubber plug 411 for aseptically sealing the joining portion of the material dispensing member 40 and the medication reservoir 41. Liquid medication in the medication reservoir 41 flows to the Venturi tube 14 via the material dispensing member 40 to intermix with the gas-water mixture. At the mixing device 15, the liquid medication in the form of aerosol is generated. A pressure regulator 150 is provided in the mixing device 15. At the end of the line 12 there is provided a heater 17 proximate to the mixing device 15 and an outlet 16 distal the mixing device 15. An adaptor 18 is provided in the outlet 16. Preferably, the medication unit 4 and the medication reservoir 41 are fastened together by threading or snapping.

A control panel 5 is provided on a surface of the housing 1 and is electrically connected to the pressure regulator 110 of the gas reservoir 11, the mixer 10, the valve 13, the medication reservoirs 41 of the medication units 4, the mixing device 15, and the heater 17 respectively so that a medical employee may operate buttons of the control panel 5 to control at least one of the pressure regulator 110 of the gas reservoir 11, the mixer 10, the valve 13, the medication reservoirs 41 of the medication units 4, the pressure regulator 150 of the mixing device 15, and the heater 17 for adjustment as detailed later.

Preferably, aseptic, non-toxic gas such as oxygen, nitrogen, hydrogen, or carbon dioxide is supplied by the gas source 20. Preferably, aseptic, non-toxic water such as alkaline water, negative ion water, or high oxygen water is supplied by the water source 30. Preferably, aseptic liquid medication is stored in the medication reservoir 41. Preferably, the aseptic liquid medication is a quantity of biological extracts.

During operation, a medical employee may operate button(s) of the control panel 5 to control the pressure regulator 110 of the gas reservoir 11 to adjust pressure of the gas reservoir 11. Also, the medical employee may operate button(s) of the control panel 5 to control the mixer 10 to adjust the mixing ratio of water and gas therein. Also, the medical employee may operate button(s) of the control panel 5 to adjust openness of the valve 13. Also, the medical employee may operate button(s) of the control panel 5 to control the quantity of the liquid medication flowing from the medication reservoirs 41 to the Venturi tubes 14. Also, the medical employee may operate button(s) of the control panel 5 to control the pressure regulator 150 so as to adjust the mixing ratio of water, gas and liquid medication in the mixing device 15. Also, the medical employee may operate button(s) of the control panel 5 to activate and control the heater 17. It is envisaged by the invention that infected or hurt skin areas of a patient can be washed aseptically using the medical apparatus.

Figure 2:
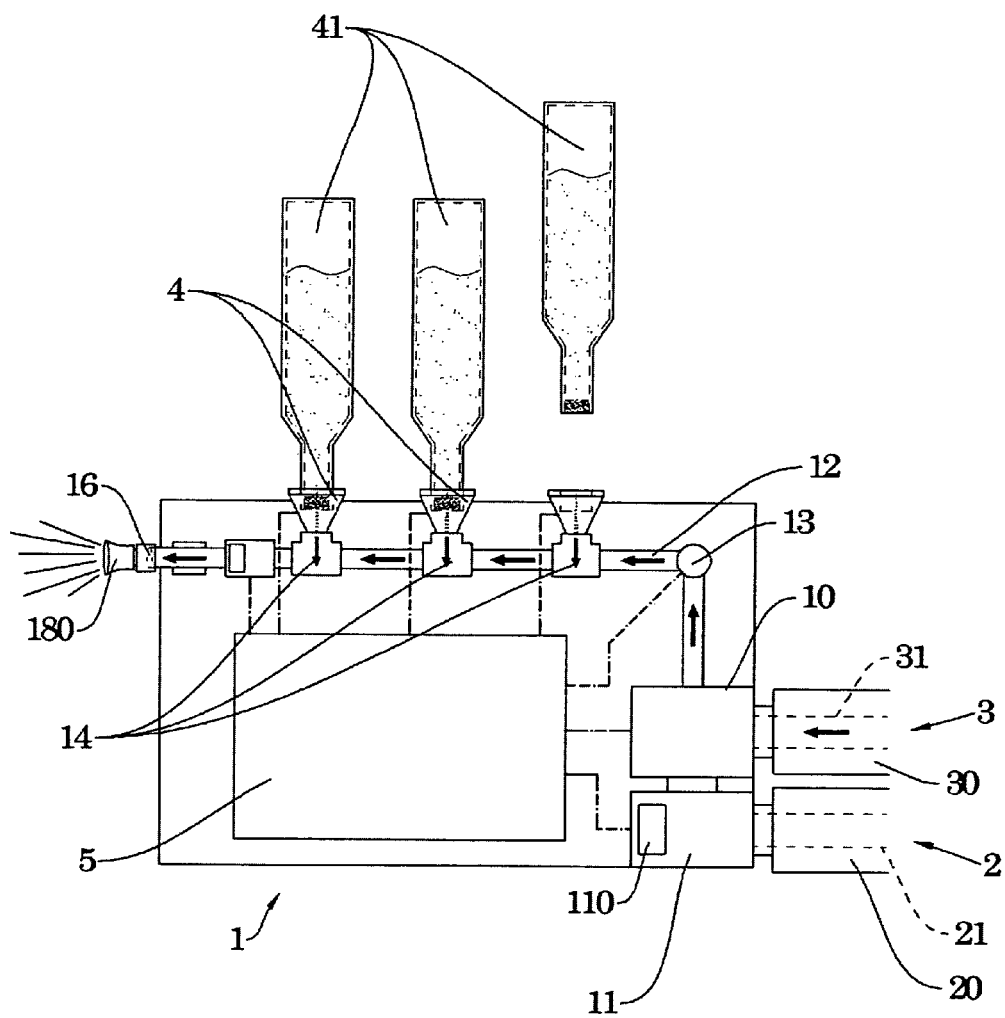
FIG. 2 schematically depicts a medical apparatus according to a second preferred embodiment of the invention.

Referring to FIG. 2, a medical apparatus in accordance with a second preferred embodiment of the invention is shown. The characteristics of the second preferred embodiment are substantially the same as that of the first preferred embodiment except the following: The adaptor 18 at the outlet 16 is replaced with an atomizer nozzle 180 which is particularly applicable to large infected or hurt skin areas of a patient.

Figure 3:
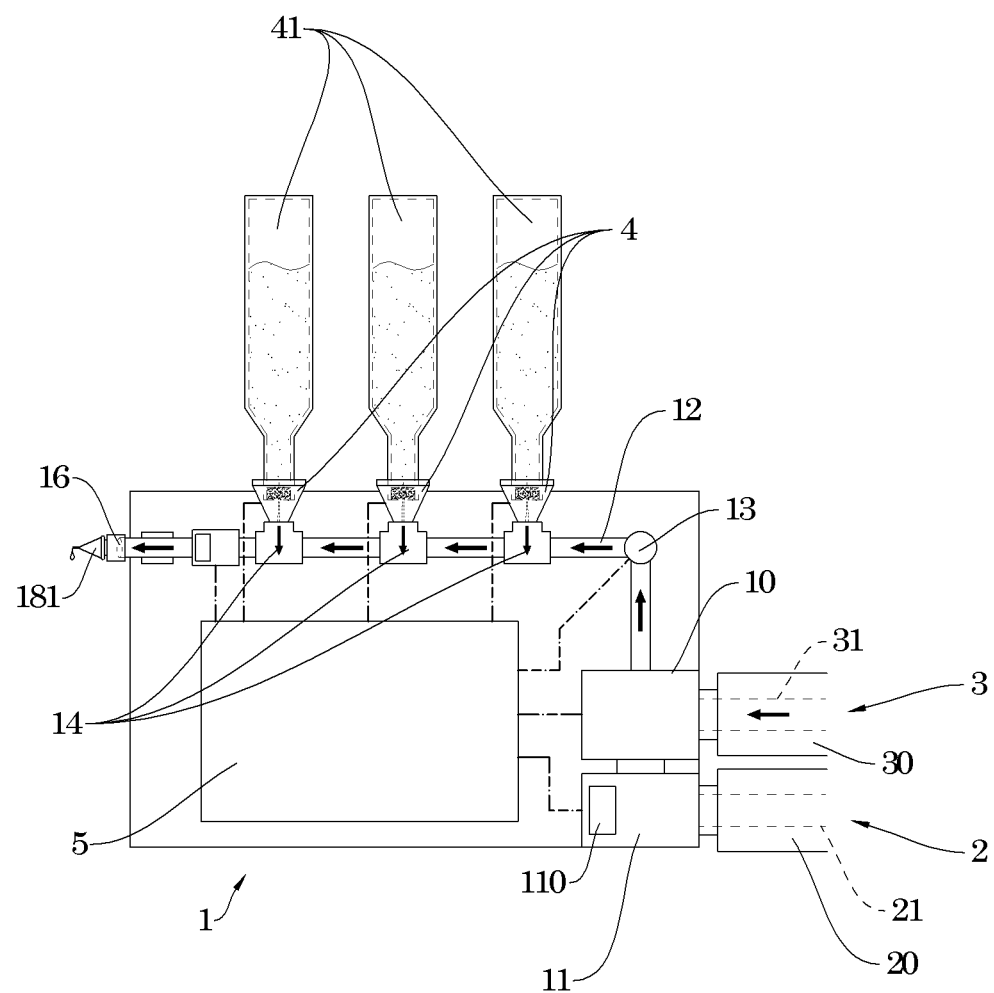
FIG. 3 schematically depicts a medical apparatus according to a third preferred embodiment of the invention.

Referring to FIG. 3, a medical apparatus in accordance with a third preferred embodiment of the invention is shown. The characteristics of the third preferred embodiment are substantially the same as that of the first preferred embodiment except the following: The adaptor 18 at the outlet 16 is replaced with a conic adaptor 181 which is particularly applicable to small infected or hurt skin areas of a patient.

Preferably, the outlet 16 and the adaptor 18, the adaptor 18 and the conic adaptor 181, or the adaptor 18 and the atomizer nozzle 180 are fastened together by threading or snapping.

While the invention has been described in terms of preferred embodiments, those skilled in the art will recognize that the invention can be practiced with modifications within the spirit and scope of the appended claims.

What is claimed is:

1. A medical apparatus comprising:

a housing;

a mixer disposed in the housing;

a gas reservoir disposed in the housing;

a water unit disposed externally of the housing and comprising a water source and a water line for flowing water from the water source to the mixer;

a gas unit disposed externally of the housing and comprising a gas source and a gas line for flowing gas from the gas source to the gas reservoir;

a gas output for flowing gas from the gas reservoir to the mixer so that gas is mixed with water to form a first mixture;

a line extending out of the mixer for carrying the first mixture;

a valve disposed on the line;

a plurality of spaced Venturi tubes disposed downstream of the valve, each of the Venturi tubes being disposed above the housing;

a plurality of medication units each comprising a medication reservoir for containing a quantity of liquid medication, each respective medication unit being in fluid communication with a corresponding one of the Venturi tubes;

a mixing device disposed downstream of the Venturi tubes to atomize the liquid medication and the first mixture to form a second mixture;

a control panel disposed on the housing and being electrically connected to the gas reservoir, the mixer, the valve, the medication reservoirs, and the mixing device respectively for control; and an outlet disposed at an end of the line and downstream of the mixing device for exiting the second mixture.

2. The medical apparatus of claim 1, further comprising a pressure regulator in the gas reservoir, the pressure regulator being controlled by the control panel.

3. The medical apparatus of claim 1, wherein each respective medication unit further comprises a material dispensing member on a bottom of the medication reservoir.

4. The medical apparatus of claim 3, wherein each respective medication unit further comprises a rubber plug for aseptically sealing a joining portion of the material dispensing member and the medication reservoir.

5. The medical apparatus of claim 1, wherein each medication unit and each medication reservoir thereof are fastened together by threading or snapping.

6. The medical apparatus of claim 1, further comprising a heater disposed between the outlet and the mixing device, the heater being electrically connected to the control panel so that the control panel controls the heater to heat the second mixture.

7. The medical apparatus of claim 1, wherein the gas is aseptic, non-toxic.

8. The medical apparatus of claim 7, wherein the aseptic, non-toxic gas is oxygen, nitrogen, hydrogen, or carbon dioxide.

9. The medical apparatus of claim 1, wherein the water is aseptic, non-toxic water.

10. The medical apparatus of claim 9, wherein the aseptic, non-toxic water is alkaline water, negative ion water, or high oxygen water.

11. The medical apparatus of claim 1, wherein the valve is a point control valve or a long control valve.

12. The medical apparatus of claim 1, wherein the liquid medication in the medication reservoirs is aseptic.

13. The medical apparatus of claim 12, wherein the aseptic liquid medication is a quantity of biological extracts.

14. The medical apparatus of claim 1, further comprising an adaptor mounted to the outlet, the adaptor being a conic adaptor or an atomizer nozzle.

15. The medical apparatus of claim 14, wherein the outlet and the adaptor are fastened together by threading or snapping.

16. The medical apparatus of claim 1, wherein the control panel controls the mixer for adjusting both gas input of the gas unit and water input of the water unit.

17. The medical apparatus of claim 1, further comprising a pressure regulator in the mixing device, the pressure regulator being controlled by the control panel.

* * * * *